United States Patent
Hoheisel

(10) Patent No.: US 8,361,263 B2
(45) Date of Patent: Jan. 29, 2013

(54) METHOD FOR PROTECTING A DISPLAY FACILITY

(75) Inventor: Martin Hoheisel, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 144 days.

(21) Appl. No.: 12/622,929

(22) Filed: Nov. 20, 2009

(65) Prior Publication Data

US 2010/0065673 A1    Mar. 18, 2010

Related U.S. Application Data

(63) Continuation of application No. 11/481,665, filed on Jul. 6, 2006, now abandoned.

(30) Foreign Application Priority Data

Jul. 8, 2005  (DE) .......................... 10 2005 032 028

(51) Int. Cl.
*B32B 37/00* (2006.01)

(52) U.S. Cl. .......... 156/229; 134/15; 242/370; 242/538; 242/410; 242/526; 341/22; 345/156; 345/173; 345/174; 345/175; 345/176; 345/177; 156/247; 156/281

(58) Field of Classification Search ........................ None
See application file for complete search history.

(56) References Cited

U.S. PATENT DOCUMENTS

| | | | |
|---|---|---|---|
| 2,859,656 A | 11/1958 | Limieux | |
| 4,542,538 A * | 9/1985 | Moretti et al. | 2/438 |
| 4,621,735 A | 11/1986 | Coon et al. | |
| 5,429,142 A | 7/1995 | Szabo et al. | |
| 5,550,564 A * | 8/1996 | Cragun | 345/173 |
| 5,765,565 A | 6/1998 | Adair | |
| 5,873,814 A | 2/1999 | Adair | |
| 5,910,356 A * | 6/1999 | Ishikawa et al. | 428/215 |
| 6,073,296 A * | 6/2000 | Bouguerfa | 15/102 |
| 6,132,367 A | 10/2000 | Adair | |
| 6,428,415 B1 * | 8/2002 | Ohba et al. | 463/31 |
| 6,845,775 B1 | 1/2005 | Barthes | |
| 2001/0040001 A1 | 11/2001 | Toyooka | |
| 2002/0114934 A1 | 8/2002 | Liu et al. | |
| 2002/0158967 A1 | 10/2002 | Janick et al. | |
| 2003/0153810 A1* | 8/2003 | Bertolero et al. | 600/101 |
| 2003/0177679 A1 | 9/2003 | Blum et al. | |
| 2004/0156100 A1 | 8/2004 | Fuchs et al. | |
| 2004/0183975 A1 | 9/2004 | Yamaguchi et al. | |

FOREIGN PATENT DOCUMENTS

| | | |
|---|---|---|
| DE | 299 04 738 U1 | 7/1999 |
| DE | 103 11 198 A1 | 8/2004 |
| EP | 0 585 000 A2 | 3/1994 |
| WO | WO 97/37581 A2 | 10/1997 |
| WO | WO 98/02107 A1 | 1/1998 |
| WO | WO 98/03013 A1 | 1/1998 |

* cited by examiner

*Primary Examiner* — Mark A Osele
*Assistant Examiner* — Nickolas Harm

(57) ABSTRACT

The invention relates to a device for protecting a display facility, comprising a protective element for covering an image surface of the display facility. As the protective element is designed to be transparent and the retaining means are provided for the exchangeable arrangement of the protective element in front of the image surface, a protective device is provided, which allows the image surface to be examined and is easy to operate.

12 Claims, 1 Drawing Sheet

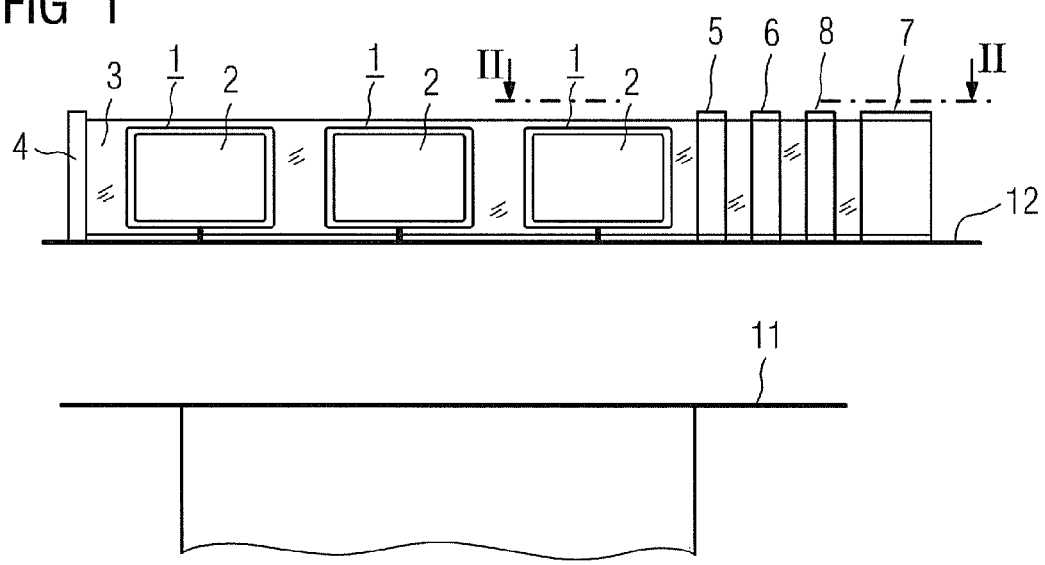
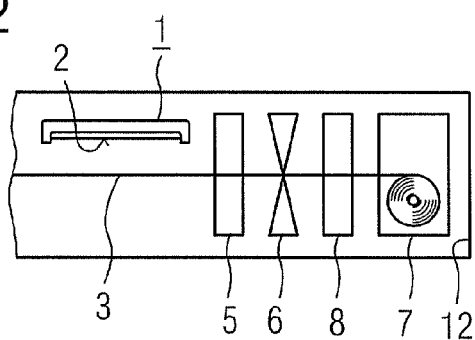
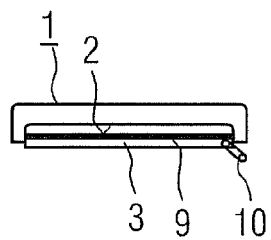
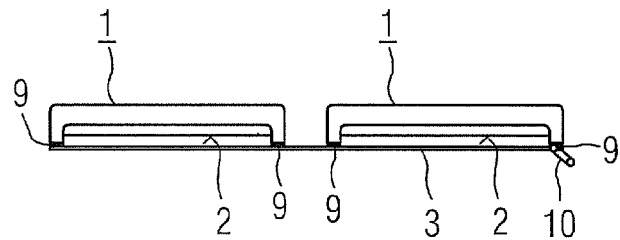

METHOD FOR PROTECTING A DISPLAY FACILITY

CROSS REFERENCE TO RELATED APPLICATIONS

This application is a continuation of U.S. application Ser. No. 11/481,665 filed Jul. 6, 2006 now abandoned. This application claims priority of German application No. 10 2005 032 028.7 filed Jul. 8, 2005. All of the applications are incorporated by reference herein in their entirety.

FIELD OF THE INVENTION

The invention relates to a device for protecting a display facility, comprising a protective element for covering an image surface of the display facility.

BACKGROUND OF THE INVENTION

In operating theatres, electronic display facilities are frequently available in the form of individual monitors or monitor lights, in order to obtain information about status changes in patients during a medical intervention. In this process, the screen surface of the display facility can be contaminated by an intervention carried out in the medical working environment, in which bodily fluids, such as blood or infusion solutions, can spray for instance. Attention must be paid to ensure a sterile environment particularly with medical interventions, in other words, a regular cleaning of the screen surface using disinfectants is essential. Nowadays it is known for this cleaning to be provided by manually disinfecting the display facility, in which liquid disinfectant is sprayed on and the image surface is wiped clean. Such a cleaning step is critical, particularly with flat screens, which are used increasingly nowadays. The direct contact involved with wiping the screen surface with the known cleaning agent can easily lead to the sensitive screen surface becoming damaged. This results in a deterioration in the image quality and thus a reduction in the quality of the status information about the patient. A gentle screen surface removal of screen contaminations is also of interest for artistic, technical and other activities subjected to contamination in conjunction with display facilities.

The utility model DE 299 04 738 U1 discloses a device for covering an object comprising a cover element completely covering the object. The cover element is arranged on a mounting frame in a moveable manner, such that this can be brought into a position covering or releasing the object. The aim of this device is to conceal and essentially improve in the simplest possible manner the optical appearance image of an object, which is neither seen nor used.

The known covering is unsuitable particularly for applications in medical engineering, in monitor lights in operating theatres for instance. The image surface cannot be read when the cover element is in a covering position. Conversely, the image surface is not protected when the cover element is in the position releasing the display facility.

SUMMARY OF THE INVENTION

The object underlying the invention is thus to provide a protective device of the type mentioned at the start, which allows the image surface to be observed and is easy to operate.

This object is achieved with the protective device of the type mentioned at the start, in that the protective element is designed to be transparent, and that the retaining means are provided in front of the image surface for the exchangeable arrangement of the protective element. The transparent protective element ensures the usability of an image surface covered therewith. An exchangeable arrangement of the protective element in front of the image surface protects this against direct contamination. If the contamination of the protective element results in the legibility of the image information being impaired, the protective element can be renewed by means of exchange, since it is fixed in an exchangeable manner. The protective element can touch the surface, or can assume a fixable distance in front of it. The protective element is advantageously designed to be two-dimensional, approximately to the size of the image surface, and can be designed for instance as a plastic or glass plate.

In a preferred embodiment of the invention, the protective element is designed as a film. A film exhibits the characteristic here in that the spatial expansion in one direction of the room dimensions is considerably smaller than the spatial expansion in the other two directions. A film is thus thin, can be rolled, folded, placed, drawn, stretched and such like and thus represents a simple and favorable realization of the protective element.

In a further advantageous embodiment of the invention, the protective element is designed to be sterilizable. The material of the protective element, for instance a plastic film, is thus able to endure a sterilization process, in other words for instance temperature budget operating in a sterilizing fashion or a chemical clean. The protective element can be provided here germ-free and can be used in particular for medical purposes, in operating theatres for instance.

In a further preferred embodiment of the invention, the protective element comprises a self-cleaning surface and/or a development-inhibiting effect for germs. The condition of the surface is designed such that a dirt and fluid accumulation is reduced. This can be achieved for instance by an anti-adhesive coating on the side of the protective element facing away from the image surface. The surface itself features a minimal roughness so as to also hamper the accumulation of genus and their growth in addition to dirt and fluid. An inhibited germ development can also be assisted by a suitable coating, an applied germ killing solution for instance.

In a further advantageous embodiment, at least one optical characteristic of the protective element is conditioned. To ensure good legibility of the image information, the dielectric function for the provided application can be optimized by selecting the material and the processing steps of the protective element, in other words, refraction index and absorption as well as the associated transmission and reflection of light through the protective element. The dielectric function can be adjusted locally. In addition, a coating, for instance an anti-reflection coating, can be applied to the film, in order to prevent disturbing reflections of light sources on the protective element, which impair the legibility of the image information.

In a further preferred embodiment variant of the invention, the retaining means comprise a dispenser for the protective element. An unused, clean protective element can be hereby passed out of the dispenser in front of the image surface. The unused protective element is folded, placed or stored in another manner in the dispenser. This allows the used protective element and/or protective element segment to be exchanged quickly in the case of the interfering contamination and thus enables an improved work flow. In addition, a rapid change in the protective element segment is also possible during a medical intervention.

In a further advantageous embodiment of the invention, the dispenser is designed as a reel, onto which the protective element designed as a film strip is rolled. The protective element can be rolled from the reel by means of traction and can be positioned in front of the image surface. The refill of the dispenser consists for instance in replacing an empty film strip reel with a film strip reel equipped with an unused protective element 3. The protective element segment and the protective element roll can be changed and exchanged rapidly in each instance, even during a medical intervention for example.

In a further preferred embodiment of the invention, the retaining means comprise a fixing device for the protective element, which work together with the dispenser to stretch the protective element. A fixing device, such as a clamp for a film for instance, can provide a level and smooth surface by means of stretching the protective element, which always ensures identically remaining image characteristics when the monitor is used with the existing protective element. The fixing device eliminates a change in the surface angle and thus the reflection characteristics by preventing the protective element from moving. A fold-free stretch state of the protective element also assists with an efficient dripping of fluids.

In a further advantageous embodiment variant of the invention, provision is made for a device for separating a used segment of the protective element designed as a film strip. Such a device can be designed for instance as a tear-off edge or a guided separation cutter. The separation device allows the used protective element to be separated from the unused part of the protective element band in a rapid and simple manner, thereby rendering a hygienic and rapid exchange of the protective element segment possible. The work flow can thus be improved and a good legibility of the image surface is ensured.

In a further preferred embodiment of the invention, the retaining means comprise a roll-up facility for the used protective element. This represents a further possibility in addition to a separation device. The used protective element is collected here on the roll-up device and can be used again, after removing the contamination or renewed conditioning, sterilization for instance, or if necessary completely decontaminated. Since the protective element is not actually used up, when the protective element is reused, this is an environmentally friendly and cost-effective solution.

In a further advantageous embodiment of the invention, provision is made for a facility for cleaning the used protective element. The cleaning can be carried out here between the display facility and the roll-up facility. It is thus possible to provide a clean and optionally conditioned protective element already at the time of the roll-up. If there is no longer a protective element in the dispenser, the rolled-up protective element in the roll-up facility can once again be fed to the dispenser and reused. Alternatively, the protective element can be designed as an endless reel, and the cleaning is carried out between carrying off the contaminated protective element of the image surface and supplying the unused protective element on the image surface. The protective element quantity requirement can be further reduced by an endless reel.

In a further preferred embodiment variant of the invention, the retaining means are designed as an adhesive layer which can be removed from the image surface. Retaining means are thus not necessary in terms of the device facility, which reduces the space required by the protective device. The adhesive layer on the protective element can be designed as a self-adhesive film, and be present in a structured form so as to adhere for instance not to the image surface itself, but instead to the housing of the display facility. A free definition of adhesive points, adhesive lines and adhesive surfaces on the protective element is possible by using glue on a protective element without an adhesive layer which can be removed from the image surface. With a suitable selection of the protective element or by a charging facility, the retaining means can be designed in the form of electrostatic forces. This is advantageous in that neither the adhesive layer, nor further mechanical components have to be provided in order to arrange the protective element in an exchangeable fashion. For an improved exchangeability of protective elements with an adhesive layer or electrostatic retaining means, provision can be made for a tab to withdraw the protective element from the image surface or the frame of the display facility. The used protective element can thus be quickly removed and can be replaced by applying a new protective element.

BRIEF DESCRIPTION OF THE DRAWINGS

Further advantages of the protective device according to the invention result from an exemplary embodiment which is described in more detail below with reference to the drawings, in which;

FIG. 1 shows a schematic representation of a protective device according to the invention for a display facility of a medical working environment, FIG. 2 shows a schematic representation of extracts of a section of FIG. 1, FIG. 3 shows a schematic representation of an alternative embodiment of the protective device from FIG. 1 with an adhesive layer covering the whole area, FIG. 4 shows a schematic representation of a variant of the exemplary embodiment from FIG. 3 with a structured adhesive layer.

DETAILED DESCRIPTION OF THE INVENTION

FIG. 1 shows a protective device according to the invention for a display device 1, such as monitors for displaying heart rates, blood pressure, ECG, EEC or visual body part displays, at a medical working environment. The display facility 1 features one or a number of screens, which are delimited by an image surface 2 of the working environment. To protect the image surface 2, a protective element 3 is available, which is arranged in the exemplary embodiment at a minimal distance in front of the image surface 2. The protective element 3 is designed as a transparent film and is prepared for use in a medical working environment by means of sterilization. As a result of the vicinity of the image surface 2 to an operating table 11, contamination of the image surface 2 by bodily fluids or secretions cannot be ruled out. The protective element 3 thus also comprises a fluid-rejecting surface, so as to reduce the ultimately remaining contamination on the protective element 3 by draining the fluid, in the case of fluid squirting onto the protective element surface. In addition, an anti-reflecting layer is applied to the side of the protective element 3 facing away from the image surface 2, so as to reduce disturbing reflections of the operating theatre lighting (not shown) in the region of the image surface 2 of the display facility 1. The protective element 3 is mounted in a dispenser 4 as a film reel roll. The dispenser 4 can be fixed here to the display facility 1, on a suitable frame 12 or another suitable fixing option such as a wall. By means of traction, the protective element 3 can be passed out of the dispenser 4 in front of the image surface 2. This can be carried out manually or with the aid of an electrical drive for instance. A fixing facility 5 for the protective element 3 can be positioned for instance on the side of the display facility 1 facing the dispensing facility 4. The options mentioned for the dispenser 4 can be transferred for securing the fixing facility 5. The protective element 3 is stretched in front of the image surface 2 by means of the fixing facility 5, in order to ensure constant examination conditions for the used protective element segment. If the contamination on the protective element 3 results in the legibility of the screen content being impaired, the contaminated protective element 3 can be removed by means of traction. The used protective element 3 is removed by means of traction and the unused protective element 3 is fed out of the dispenser 4 at the same time. The used protective element 3 can be removed from the unused protective element 3 by means of a separation device 6, for instance, in which the used protective element 3 is passed over a tear-off edge or a cutting facility. If the used protective element 3 is mechanically undamaged, this must not necessarily be removed by a separation device 6. Instead it can by gathered by a roll-up facility 7, so as to reuse it subsequently after removing the contamination and renewing the conditioning. The roll-up facility 7 for the used protective element 3 can also function here as a fixing device 5. In the presence of a roll-up facility 7, the use of a cleaning facility 8 advantageously proves itself, which can be arranged for instance between fixing device 5 and roll-up facility 7. The cleaning facility 8 enables a cleaned and optionally conditioned protective element 3 to be rolled up in the roll-up facility 7. The protective element 3 wound up in the roll-up facility 7 can be directly fed to the dispenser 4 if necessary.

In FIG. 2, the arrangement of the display facility 1, frame 12, fixing device 5, separation device 6, cleaning facility 8 and roll-up facility 7 is shown as an enlarged cross-section. The said means as well as the dispenser 4 can be fixed to the frame 12. The use of a roll-up facility 7 allows the fixing device 5 and the separation device 6 to be removed for instance, since the roll-up facility 7 can assume the function of the fixing device 5, and a separation of the protective element is only necessary in exceptional cases, namely when the protective element 3 is mechanically damaged. For this purpose, a separation device 6 can be an integral part of the roll-up facility 7.

Possible variants of the protective device with a minimal space requirement are shown in FIG. 3 and FIG. 4. The image surface 2 of the display facility 1 is protected by a protective element 3 which comprises an adhesive layer 9 which can be removed from the image surface 2. In this exemplary embodiment, the protective element 3 can be designed as a film. The adhesive layer 9 can be present on the protective element 3 over the whole surface or also in a structured fashion.

In FIG. 3, the size of the protective element 3 is adjusted to the size of the image surface 2 and can be directly applied to the image surface 2. The adhesive layer 9 adheres the protective element 3 to the image surface 2 and protects this against contamination. If the contamination of the protective element 3 results in a reduction in the legibility of the image contents, the protective element 3 can be easily detached from the image surface with the aid of a tab 10 and can be replaced by a new protective element 3.

Alternatively, in FIG. 4 the protective element 3 is dimensioned larger than the image surface 2, approximately to the size of the frame of the display facility 1, and is structured with an adhesive layer 9, and in fact such that the adhesive points of the protective element 3 correspond to the screen frame dimensions of the display facility 1. The protective element 3 is accommodated in front of the image surface 2 and thus fixed so that it completely adheres to the screen frame for instance. The protective element 3 can only cover a partial front of the display facility 1 or the entire front of the display facility 1. If an interfering contamination of the protective element 3 occurs by blood spraying for instance, the protective element 3 can be removed from screen frames of the display facility 1 with the aid of a tab 10, and can be replaced by a new protective element 3.

The invention claimed is:

1. A method for avoiding contamination of one or more electronic image display surfaces during a medical intervention performed in an operating theatre, comprising:
   continually providing a transparent and clean protective film over the one or more image display surfaces in the operating theatre while allowing the one or more image display surfaces to be observed during the medical intervention, including forming the film as a sheet with sufficient length so that different portions of the same sheet can be sequentially positioned over the one or more display surfaces thereby allowing a user to repeatedly cover and protect the one or more display surfaces multiple times with different clean portions of the sheet during the medical intervention;
   providing a reel, positioned adjacent the one or more display surfaces;
   rolling the sheet onto the reel for storage and for sequentially dispensing portions of the sheet from the reel to repeatedly cover the one or more display surfaces with clean portions of the sheet;
   providing a receiving device positioned adjacent one of the one or more display surfaces, and spaced away from the reel so that portions of the sheet extend between the reel and the receiving device, positioned to cover the one or more display surfaces; and
   rolling used portions of the sheet onto the receiving device;
   wherein the transparent and clean protective film is positioned at a fixable distance in front of the image display surfaces such that the protective film and the image display surfaces are not in mutual contact during the continually providing step.

2. The method as claimed in claim 1, wherein the film includes an anti-reflection coating to mitigate reflections from a light source in the operating theatre on the protective film.

3. The method as claimed in claim 1, further including providing a cleaning facility positioned to receive used portions of the film after the used portions have covered the one or more display surfaces and cleaning the used portions and then feeding the cleaned used portions through the reel for re-use.

4. The method as claimed in claim 1, including providing the receiving device with a fixing device cooperatively operating with the reel to stretch the protective film.

5. The method as claimed in claim 1, further including positioning a separating device between the receiving device and the reel for separating a used portion of the protective film from the sheet.

6. The method as claimed in claim 1, wherein the transparent and clean protective film is a size of the one or more image display surfaces.

7. The method as claimed in claim 1, further comprising preventing the transparent and clean protective film from moving, to eliminate a change in a surface angle and a change in a reflection characteristic of the transparent and clean protective film.

8. The method as claimed in claim 1, further comprising applying an anti-reflective layer to a side of the transparent and clean protective film facing away from the image display surface.

9. The method as claimed in claim 1, further comprising:
   providing a plurality of said image display surfaces;
   providing a frame of said image display surfaces, each image display surface attached to the frame;

wherein said providing the reel comprising fixing the reel to the frame.

10. The method as claimed in claim 9, further comprising:
adhering the clean portions of the sheet at adhesive points with an adhesive layer to the frame such that the clean portions of the sheet are positioned at the fixable distance in front of the image display surfaces.

11. The method as claimed in claim 10, further comprising:
removing the used portions of the sheet from the frame; and replacing the used portions of the sheet with clean portions of the sheet that are adhered to the frame.

12. The method as claimed in claim 1, further comprising:
providing a fixing facility positioned between the reel and the receiving device;
stretching the protective film in front of the one or more image display surfaces with the fixing facility.

* * * * *